United States Patent [19]

Chipkin et al.

[11] Patent Number: 5,104,814
[45] Date of Patent: Apr. 14, 1992

[54] ASSAY KIT AND METHODS FOR NEUROLEPTIC DRUGS

[75] Inventors: Richard Chipkin, West Caldwell; Robert D. McQuade, Scotch Plains, both of N.J.

[73] Assignee: Schering Corporation, Kenilworth, N.J.

[21] Appl. No.: 631,220

[22] Filed: Dec. 21, 1990

Related U.S. Application Data

[63] Continuation of Ser. No. 274,589, Nov. 22, 1988, abandoned.

[51] Int. Cl.$^5$ .................. G01N 33/567; C07D 223/16
[52] U.S. Cl. .................................... 436/504; 436/501; 436/503; 540/576
[58] Field of Search ................. 424/1.1; 436/501, 503, 436/504, 518, 536, 547

[56] References Cited

U.S. PATENT DOCUMENTS 4,760,029  7/1988  Barnett et al. ...................... 436/504

FOREIGN PATENT DOCUMENTS 0230270  7/1987  European Pat. Off. .

OTHER PUBLICATIONS

Iorio et al., J. Pharm. Exp. Ther., vol. 226, No. 2, pp. 462–468 (1983).
Chipkin et al., J. Pharm. Exp. Ther., vol. 247, No. 3, pp. 1093–1102 (1988).
McQuade et al., J. Pharm. Exp. Ther., vol. 257, No. 1, pp. 42–48 (1991).

*Primary Examiner*—Mary E. Ceperley
*Attorney, Agent, or Firm*—Anita W. Magatti; Warrick E. Lee, Jr.; Edward H. Mazer

[57] ABSTRACT

The invention describes a kit and a method useful for analyzing the plasma concentration of an active neuroleptic drug known to have D-1 receptor antagonist properties utilizing labeled [−]trans 6,7,7a,8,9,13b-hexahydro-3-chloro-2-hydroxy-N-methyl-5H-benzo[d]naphtho-[2,1-b]-azepine.

15 Claims, No Drawings

& G. V. Trabucchi eds. Raven Press, New York, pages 73-93 (1978)].

ASSAY KIT AND METHODS FOR NEUROLEPTIC DRUGS

This is a continuation of application Ser. No. 07/274,589 filed Nov. 22, 1988, now abandoned.

BACKGROUND OF THE INVENTION

A report in the recent literature has described the antipsychotic, antidepressant and sedative activities of compounds known as hexahydro-benzo[d]naphtho[2,1-b]azepines (European Patent Application No. 230270). These compounds include [-]trans 6,7,7a,8,9,13b-hexahydro-3-chloro-2-hydroxy-N-methyl-5H-benzo[d]naphtho-[2,1-b]-azepine.

Other antipsychotic drugs such as R-(+)-8-chloro-2,3,4,5-tetrahydro-3-methyl-5-phenyl-1H-3-benzazepine-7-ol have been shown to be selective binders of dopamine D-1 receptors (J. Pharmacol. Exp. Ther., 226: 462 (1983)). This selectivity is reported to be 2500 fold or virtually to the exclusion of the dopamine D-2 receptors. Such specificity indicates that the compound may possess unusual antipsychotic effects and low liability for producing side effects such as extrapyramidal effects in humans. This is so because D-1 receptor antagonism like D-2 receptor antagonism is associated with antipsychotic effects in laboratory animal models but D-2 receptor antagonism is also associated with the untoward side-effects characteristic of most known neuroleptics (e.g., hyperprolactinemia in animals and humans).

Tritiated R-(+)-8-chloro-2,3,4,5-tetrahydro-3-methyl-5-phenyl-1H-3-benzazepine-7-ol has also been used in a method of determining the level of D-1 antagonism of a neuroleptic drug. See U.S. Pat. No. 4,760,029.

SUMMARY OF THE INVENTION

It has been found that tritiated [−]trans-6,7,7a,8,9,13b-hexahydro-3-chloro-2-hydroxy-N-methyl-5H-benzo[d]naphtho-[2,1-b]-azepine provides an advantageous method for determining the level of D-1 antagonism of a neuroleptic drug e.g. in a plasma sample, and is a potent D-1 specific binder.

One aspect of the present invention is a labelled form of [−]trans 6,7,7a,8,9,13b-hexahydro-3-chloro-2-hydroxy-N-methyl-5H-benzo[d]naptho-[2,1-b]-azepine. A preferred label is a radioactive label. More preferably the radioactive label will be tritium. Most preferably the tritium label will be one or more of the N-methyl hydrogens.

The invention also involves a method of determining the level of D-1 antagonism of a neuroleptic drug in a plasma sample or of a test compound comprising:

(a) contacting said plasma sample or a test compound with mammalian tissue having D-1 receptor sites therein to form neuroleptic drug D-1 receptor complexes;

(b) adding labelled [−]trans 6,7,7a,8,9,13b-hexahydro-3-chloro-2-hydroxy-N-methyl-5H-benzo[d]naphtho[2,1-b]-azepine to the mammalian tissue, (c) measuring the amount of labelled [−]trans 6,7,7a,8,9,13b-hexahydro-3-chloro-2-hydroxy-N-methyl-5H-benzo[d]naphtho-[2,1-b]-azepine complexed with D-1 receptors; and (d) correlating the amount of labelled [−]trans 6,7,7a,8,9,13b-hexahydro-3-chloro-2-hydroxy-N-methyl-5H-benzo[d]naphtho-[2,1-b]-azepine complexed with said D-1 receptors to the level of said D-1 antagonism of said neuroleptic drug.

The labelled [−]trans 6,7,7a,8,9,13b-hexahydro-3-chloro-2-hydroxy-N-methyl-5H-benzo[d]naphtho-[2,1-b]azepine can be mixed with the test compound or the plasma sample, then contacted with the mammalian tissue containing D-1 receptors prior to measurement and correlation of the amount of the labelled compound.

Preferably, the [-]trans 6,7,7a,8,9,13b-hexahydro-3-chloro-2-hydroxy-N-methyl-5H-benzo[d]naphtho-[2,1-b]-azepine will be comprised of an enriched level of radioactive atoms, more preferably by tritium (3H) atoms located on the N-methyl substituent.

Another aspect of the invention involves a kit, which is useful for estimating the levels of a neuroleptic drug that is a potent D-1 antagonist present in mammalian plasma; said kit comprising:

(a) A sample of purified mammalian tissue and;

(b) A sufficient amount of labelled [-]trans 6,7,7a,8,9,13b-hexahydro-3-chloro-2-hydroxy-N-methyl-5H-benzo[d]naphtho-[2,1-b]-azepine to perform one analytic procedure.

In a preferred kit of the invention, the labelled [-]trans 6,7,7a,8,9,13b-hexahydro-3-chloro-2-hydroxy-N-methyl-5H-benzo[d]naphtho-[2,1-b]-azepine will be comprised of an enriched level of radioactive atoms, preferably tritium atoms located on the N-methyl substituent, in order to facilitate the measurement of the relative binding affinity values.

DETAILED DESCRIPTION OF THE INVENTION

The compound, [-]trans 6,7,7a,8,9,13b-hexahydro-3-chloro-2-hydroxy-N-methyl-5H-benzo[d]naphtho[2,1-b]-azepine (hereinafter referred to as Compound) may be prepared by the method as described in European Patent Application No. 230270 (published on July 29, 1987) or U.S. patent application Ser. No. 226304 filed July 29, 1988 (which are hereby incorporated by reference) or by other art recognized methods. The Compound possesses in vivo and in vitro antidopaminergic effects markedly different than those of standard antipsychotic drugs.

Label is meant to include any marker attached or recognized on a molecule so as to confer an ability to distinguish that molecule from the unmarked or naturally occurring Compound. Examples of such labels include enzyme, fluorescent, luminescent, antibody and enriched levels of radioactivity. Titrating test samples or test compounds to or with the labelled Compound in the presence of mammalian tissue containing D-1 receptors will produce a competition binding profile, which when compared with a standard, will provide information about the D-1 binding activity of the test sample (e.g. plasma) or test compound. The mammalian tissue may be contacted with the test sample or test compound followed by addition of the labelled Compound; the mammalian tissue may be contacted with the labelled Compound followed by addition of the test sample or test compound; or the test sample or test compound may be mixed with the labelled Compound followed by contacting the mixture with mammalian tissue having D-1 receptors. D-1 receptor containing tissues in mammals include retina, parathyroid, vascular smooth muscle and adrenal glomerulosa [Memomissale et al., J. Neuro. Tr. 22:19-32 (1986)]; renal vasculature [Fredrickson et al., Am. J. Physiol. 249:F236-F240 (1985)]; kidney [Barnett et al., *Central and Peripheral Dopamine Receptors: Biochemistry and Pharmacology*, P. F. Spano et al., editors, Fidia Research Series: Symposium in Neuroscience, Vol. 5, Liviana Press, Padova, Italy (1988)]; and brain. Any sequence of mixing and contacting will provide the necessary binding of labelled Compound for measurement. Preferably the mammalian tissue is added after the mixing of the labelled Compound and test sample or test compound. This procedure will be useful for screeningpotential drugs for D-1 activity as well as determining the levels of D-1 activity in a serum, plasma or other test sample.

Labelling the Compound with an enzyme, fluorescent, luminescent, antibody, radioactive or tritium ($^3$H) label so as not to alter the binding properties of the receptor can be accomplished by techniques available in the art. The labelled forms of [—]trans 6,7,7a,8,9,13b-hexahydro-3-chloro-2-hydroxy-N-methyl-5H-benzo[d]naphtho-[2,1-b]-azepine may be obtained by exchanging labelled atoms for unlabelled atoms using exchange techniques known in the art. The labelled Compounds may also be obtained by using labelled reagents during the preparation of the Compound such that labelled atoms are incorporated into the Compound during synthesis. Labelled Compounds may also be obtained by converting certain compounds of European Patent Application No. 230270 to other compounds of the same Patent Application using available and known labelled reagents in reactions known to those skilled in the art. For example, [—]trans 6,7,7a,8,9,13b-hexahydro-3-chloro-2-hydroxy-N-desmethyl-5H-benzo[d]naphtho-[2,1-b]azepine can be converted to [N-methyl-$^3$H] Compound with tritiated methyliodide using techniques well known to one skilled in the art, e.g. mixture of reagents for about 2 hours at about room temperature.

Because of this unique profile and a recognition of the potential utility and advantages of a radiolabelled form of the Compound as a specific D-1 receptor ligand, [N-methyl-$^3$H] Compound was synthesized. Prior to this, a labelled form of R-(+)-8-chloro-2,3,4,5-tetrahydro- 3-methyl-5-phenyl-1H-3-benzazepine-7-ol has been used to label the D-1 receptor. B. Billard and colleagues (Life Sciences 35, 188 (1984)). The studies described here were undertaken to characterize the binding properties of [N-methyl-$^3$H] Compound in rat striatum and to define its specificity based on competition studies with selected drugs. The methods are a modification of those described in a paper by B. Billard and colleagues (Life Sciences 35, 1885 (1984)), which is incorporated herein by reference.

Tissue Preparation

Male Sprague-Dawley rats (200 to 250 g) from Charles River Breeding Laboratories, Mass. were used to obtain brain tissue. The rats were decapitated, their brains removed and placed on ice. Striatal tissue was excised, pooled, and homogenized (Brinkman Polytron, 10 sec) in 100 volumes (v/v) of ice cold 50mM Tris-HCl buffer, pH 7.4 (at 25° C.). The homogenate was centrifuged at 20,000×g for 10 min. The resultant pellet was rehomogenized in Tris-HCl buffer and centrifuged again. The final pellet was resuspended in 50 mM Tris-HCl buffer pH 7.4 containing 120 mM NaCl, 5 mM KCL, 2 mM CaCl$_2$, and 1 mM MgCl$_2$.

Assay

Polypropylene incubation tubes (in triplicate) received 100 μl of various concentrations of drugs dissolved or suspended in 0.05 M Tris-HCl buffer, pH 7.4, containing 4 mg/ml methylcellulose, 100 μl of a solution of [N-methyl-$^3$H] Compound in Tris-HCl buffer (final reaction mixture concentration=1.0 nM) and 800 μl of tissue suspension (3 mg/assay). At a ligand concentration of approximately 1.0 nM, binding was found in preliminary experiments to be a linear function of tissue concentration up to 8 mg per assay. Tubes were incubated at ambient temperature (approx. 23° C.) for 25 min and rapidly filtered under vacuum through Whatman GF/B filters with four 4-ml rinses of ice-cold 50 mM Tris-HCl buffer, pH 7.4. The filters were monitored for radioactivity through liquid scintillation counting in Scintosol (Isolab, Inc.).

Results

Parameters of [N-methyl-$^3$H] Compound Binding in Rat Striatum

When binding was evaluated as a function of radioligand concentration, saturation of specific sites was clearly achieved while non-specific binding was minimal. Analysis of these data revealed that labelled Compound exhibited a $K_D$ (disassociation constant) of 1.7 nM.

To test the receptor specificity of [N-methyl-$^3$H] Compound, competition curves were generated for a variety of pharmacologically active drugs using [N-methyl-$^3$H] Compound as the radioligand. The unlabelled Compound inhibited the binding of the labelled Compound with a $K_I$ of 3.6 nM. The effects were stereoselective as evidenced by the greatly reduced potency of the cisisomer of Compound. Dopamine yielded a biphasic inhibition curve with $K_I$ (inhibition constant) values of 0.2 and 2.6 μM. The high affinity sites are converted to low affinity by addition of 0.1 mM GPP(NH)P (5'-guanylylimidodiphosphate), with all sites exhibiting a single $K_I$ of 2.4 μM.

In vivo, [N-methyl-$^3$H] Compound labels rat striatal membranes with optimal binding 1 hour after subcutaneous injection. This labeling exhibits both pharmocological specificity (1 umole of the D-1 specific compound R-(+)-8-chloro-2,3,4,5-tetrahydro-3-methyl-5-phenyl-1H-3-benzazepine-7-ol inhibits 90% of the striatal binding) and tissue selectivity (specific cerebellar levels are less than 5% of specific striatal levels).

These data indicate that Compound binds stereospecifically with high affinity to a single site in rat striatum and suggest that this site is the D-1 receptor site.

The use of [N-methyl-$^3$H] Compound for studying D-1 receptor function in the future offers several advantages. Because of its strong specificity for what appear to be D-1 sites, D-2 sites are virtually unoccupied at the [N-methyl-$^3$H] Compound ligand concentration of 1.0 nM normally used in these assays. Other advantages include its lack of adsorption onto glass and plastic surfaces and low levels of non-specific relative to total binding. The recoverable radioactivity from the polypropylene tubes used in these experiments was found to be 97%. With respect to non-specific binding, at the normally employed [N-methyl-$^3$H] Compound ligand concentration of 1.0 nM, such binding constituted only 4–8% of total binding. For comparison, non-specific binding of about 66% and 74% of total binding has been reported for $^3$H-piflutixol and $^3$H-flupentixol, respectively [Life Sciences 23, 551 (1978)].

In conclusion, [N-methyl-$^3$H] Compound is an excellent probe for studying the D-1 dopamine receptor. Clear advantages over other radioligands currently used for this purpose include receptor specificity, low non-specific binding and lack of adsorption onto assay tube surfaces.

When the labelled form of the Compound is titrated with other suspected D-1 active compounds in the presence of mammalian tissue having D-1 receptors, the competitive binding profile, as evidenced by the decrease in measurement of the radioactive label, provides information about their amount and strength of binding activity when compared to similar binding profiles for known D-1 active compounds. Advantage may also be taken of the D-1 binding properties of labelled Compound to analyze for the presence and amount of D-1 binding activity in a test sample (plasma, serum, saliva, urine, etc.) obtained from a patient. For example, various dilutions of a sample are mixed with mammalian tissue (containing D-1 receptors), preferably mammalian brain tissue, in the presence of a low concentration of labelled Compound. After incubation, the level of tissue bound label is determined for each concentration, a binding curve is constructed, and comparison is made to a binding curve for a known D-1 active compound.

Thus, a kit which contains a sample of purified rat brain membranes and an amount of radiolabeled Compound may be utilized to perform such a clinical analysis. A small plasma sample (less than 100µl) can be used and the amount of radioactivity bound to brain membranes in the presence versus absence of plasma sample from a treated patient is the measure. The basic premise is that the amount of radioactivity displaced from brain recepoors is proportional to the concentration of active drug in plasma which in turn determines therapeutic activity in Schizophrenia. The key to this assay is to have an active neuroleptic in radioactive form, with high specific activity (high radioactive counts/millimole of drug). A recent clinical reference [Psychopharmacology 82, 194 (1984)] further describes the outlined procedure.

All references herein disclosed are hereby incorporated by reference for their pertinent teachings.

We claim:

1. A method of determining the level of D-1 receptor antagonism of a neuroleptic drug in a plasma sample comprising:
    (a) contacting s id plasma sample with mammalian tissue having D-1 receptor sites therein to form neuroleptic drug D-1 receptor complexes;
    (b) adding labelled [—]trans 6,7,7a,8,9,13b-hexahydro-3-chloro-2-hydroxy-N-methyl-5H-benzo[d-]naphtho2,1-b]-azepine to the mammalian tissue,
    (c) measuring the amount of labelled [—]trans 6,7,7a,8,9,13b-hexahydro-3-chloro-2-hydroxy-N-methyl-5H-benzo[d]naphtho-[2,1-b]-azepine complexed with D-1 receptors; and
    (d) correlating the amount of labelled [—]trans 6,7,7a,8,9,13b-hexahydro-3-chloro-2-hydroxy-N-methyl-5H-benzo[d]naphtho-[2,1-b]-azepine complexed with said D-1 receptors to the level of said D-1 receptor antagonism of said neuroleptic drug.

2. The method of claim 1 wherein said labelled [—]trans 6,7,7a,8,9,13b-hexahydro-3-chloro-2-hydroxy-N-methyl-5H-benzo[d]naphtho-[2,1-b]-azepine comprises an enriched level of radioactive atoms.

3. The method of claim 2 wherein the radioactive [—]trans 6,7,7a,8,9,13b-hexahydro-3-chloro-2-hydroxy-N-methyl-5H-benzo[d]naphtho-[2,1-b]-azepine comprises an enriched level of tritium atoms located on the N-methyl substituent.

4. A method of analyzing a test compound for D-1 receptor antagonistic activity comprising:
    (a) contacting mammalian tissue containing D-1 receptors with said test compounds to form test compound D-1 receptor complexes;
    (b) adding labelled [-]trans 6,7,7a,8,9,13b-hexahydro-3-chloro-2-hydroxy-N-methyl-5H-benzo[d]naphtho[2,1-b]-azepine to the mammalian tissue,
    (c) measuring the amount of labelled [—]trans 6,7,7a,8,9,13b-hexahydro-3-chloro-2-hydroxy-N-methyl-5H-benzo[d]naphtho-[2,1-b]-azepine complexed with D-1 receptors; and
    (d) correlating the amount of [—]trans 6,7,7a,8,9,13b-hexahydro-3-chloro-2-hydroxy-N-methyl-5H-benzo[d]naphtho-[2,1-b]-azepine complexed with said D-1 receptors to the level of said D-1 receptor antagonism of said test compound.

5. The method of claim 4 wherein said labelled [—]trans 6,7,7a,8,9,13b-hexahydro-3-chloro-2-hydroxy-N-methyl-5H-benzo[d]naphtho-[2,1-b]-azepine comprises an enriched level of radioactive atoms.

6. The method of claim 5 wherein the radioactive [-]trans 6,7,7a,8,9,13b-hexahydro-3-chloro-2-hydroxy-N-methyl-5H-benzo[d]naphtho-[2,1-b]-azepine comprises an enriched level of tritium atoms located on the N-methyl substituent.

7. A method of determining the level of D-1 receptor antagonism of a neuroleptic drug in a plasma sample comprising:
    (a) mixing said plasma sample with labelled [—]trans 6,7,7a,8,9,13b-hexahydro-3-chloro-2-hydroxy-N-methyl-5H-benzo[d]naphtho-[2,1-b]-azepine to form a mixture;
    (b) contacting said mixture with mammalian tissue having D-1 receptor sites;
    (c) measuring the amount of labelled [—]trans 6,7,7a,8,9,13b-hexahydro-3-chloro-2-hydroxy-N-methyl-5H-benzo[d]naphtho-[2,1-b]-azepine complexed with D-1 receptors; and
    (d) correlating the amount of labelled [—]trans 6,7,7a,8,9,13b-hexahydro-3-chloro-2-hydroxy-N-methyl-5H-benzo[d]naphtho-[2,1-b]-azepine complexed with said D-1 receptors to the level of said D-1 receptor antagonism of said neuroleptic drug.

8. The method of claim 7 wherein said labelled [—]trans 6,7,7a,8,9,13b-hexahydro-3-chloro-2-hydroxy-N-methyl-5H-benzo[d]naphtho-[2,1-b]-azepine comprises an enriched level of radioactive atoms.

9. The method of claim 8 wherein the radioactive [—trans 6,7,7a,8,9,13b-hexahydro-3-chloro-2-hydroxy-N-methyl-5H-benzo[d]naphtho-[2,1-b]-azepine comprises an enriched level of tritium atoms located on the N-methyl substituent.

10. A method of analyzing a test compound for D-1 receptor antagonistic activity comprising:
    (a) mixing said test compound with labelled [—]trans 6,7,7a,8,9,13b-hexahydro-3-chloro-2-hydroxy-N-methyl-5H-benzo[d]naphtho-[2,1-b]-azepine to form a mixture;
    (b) contacting said mixture with mammalian tissue having D-1 receptor sites;
    (c) measuring the amount of labelled [—]trans 6,7,7a,8,9,13b-hexahydro-3-chloro-2-hydroxy-N-methyl- 5H-benzo[d]naphtho-[2,1-b]-azepine complexed with D-1 receptors; and
    (d) correlating the amount of [—]trans 6,7,7a,8,9,13b-hexahydro-3-chloro-2-hydroxy-N-methyl-5H-benzo[d]naphtho-[2,1-b]-azepine complexed with said D-1 receptors to the level of said D-1 receptor antagonism of said test compound.

11. The method of claim 10 wherein said labelled [−]trans 6,7,7a,8,9,13b-hexahydro-3-chloro-2-hydroxy-N-methyl-5H-benzo[dμl]naphtho-[2,1-b]-azepine comprises an enriched level of radioactive atoms.

12. The method of claim 11 wherein the radioactive [-μl]trans 6,7,7a,8,9,13b-hexahydro-3-chloro-2-hydroxy-N-methyl-5H-benzo[d]naphtho-[2,1-b]-azepine comprises an enriched level of tritium atoms located on the N-methyl substituent.

13. A kit useful for estimating the levels of a neuroleptic drug which is a potent D-1 receptor antagonist present in mammalian plasma comprising:

(a) a sample of purified mammalian tissue having D-1 receptor sites and;

(b) a sufficient amount of labelled [−]trans 6,7,7a,8,9,13b-hexahydro-3-chloro-2-hydroxy-N-methyl-5H-benzo[d]naphtho-[2,1-b]-azepine to perform one analytic procedure.

14. The kit defined in claim 13 wherein, the [−trans 6,7,7a,8,9,13b-hexahydro-3-chloro-2-hydroxy-N-methyl-5H-benzo[d]naphtho-[2,1-b]-azepine will be comprised of an enriched level of radioactive atoms in order to facilitate the measurement of the relative binding affinity values.

15. The kit defined in claim 14 wherein, the [−]trans 6,7,7a,8,9,13b-hexahydro-3-chloro-2-hydroxy-N-methyl-5H-benzo[d]naphtho-[2,1-b]-azepine will be comprised of an enriched level of tritium (3H) atoms located on the N-methyl substituent.

* * * * *